United States Patent [19]

Head

[11] Patent Number: 4,572,194
[45] Date of Patent: Feb. 25, 1986

[54] DEVICE FOR THERAPY OF THE HUMAN OR ANIMAL BODY

[76] Inventor: Edwin L. Head, Great Swifts, Cranbrook, Kent, England

[21] Appl. No.: 539,238

[22] Filed: Oct. 5, 1983

[30] Foreign Application Priority Data

Oct. 5, 1982 [GB] United Kingdom ............ 8228406

[51] Int. Cl.⁴ .............................................. A61N 1/02
[52] U.S. Cl. ................................................ 128/419 R
[58] Field of Search ............... 128/303.17, 303.18, 128/362, 419 R, 419 D, 419 S, 419 N, 421–423; 231/2 E; 273/84 ES

[56] References Cited

U.S. PATENT DOCUMENTS

| | | | |
|---|---|---|---|
| 3,625,222 | 12/1971 | Shimizu | 273/84 ES |
| 3,769,985 | 11/1973 | Fujii et al. | 128/419 R |
| 3,980,085 | 9/1976 | Ikuno | 128/422 |
| 4,023,573 | 5/1977 | Pantridge et al. | 128/419 D |
| 4,057,064 | 11/1977 | Morrison, Jr. et al. | 128/303.17 |
| 4,093,975 | 6/1978 | Roberts | 128/419 R |
| 4,109,660 | 8/1978 | Nesmeyanov et al. | 128/419 R |

FOREIGN PATENT DOCUMENTS

1063293 8/1959 Fed. Rep. of Germany ... 128/419 N

*Primary Examiner*—William E. Kamm
*Assistant Examiner*—Mitchell J. Shein
*Attorney, Agent, or Firm*—Sughrue, Mion, Zinn, Macpeak & Seas

[57] ABSTRACT

An electrical therapy device comprises a needle-like probe connected to a source of low current, high voltage electrical discharge. The probe can be placed in skin contact with a patient to introduce a stream of negative charge into the anatomy of the patient in order to effect relief, and in some cases cure, of inflammatory ailments.

10 Claims, 11 Drawing Figures

DEVICE FOR THERAPY OF THE HUMAN OR ANIMAL BODY

BACKGROUND OF THE INVENTION

The invention relates to a device for therapy of the human or animal body by discharge of electricity into body tissues.

Electrical discharge devices are known for use in therapeutic practices. In general, however, such devices are employed to ionize air for inhalation and no such devices are known which discharge electrical energy directly into the tissues by electrical contact of the skin of a patient with an electrode for the purpose of correcting electrical imbalance.

SUMMARY OF THE INVENTION

According to the invention, there is provided a device for electrical therapy of the human or animal body by application thereto of an electrical discharge, the device comprising electrical discharge generation means and an electrode mounted to a manually grippable member and so disposed that said electrode and the skin surface of a patient are in contact or at least in electrically conductive proximity when a skin contact surface of the member is disposed in skin contact with a patient. During use, the electrode assumes a negative electric charge and serves to provide electrons directly to body tissue.

In preferred forms of the invention, said manually grippable member defines a housing in which said discharge generation means is disposed.

Conveniently, surfaces of the member define a cavity which is open at an extremity thereof and has said electrode disposed therein and exposed through the open extremity. For instance, the electrode may extend substantially along the axis of the cavity to a point proximate the opening.

In a preferred embodiment of the invention, the device comprises a manually grippable member which defines a housing having an open recess defined in a skin contact surface of the member, and an electrode disposed in said recess and exposed so as to be in contact with or juxtaposed with respect to the skin of a patient when the aforesaid surface is in skin contact, a transformer being provided in said housing and electrically connected to said electrode, and electrical power supply means such as a battery being provided in said housing in electrical connection with the transformer. Of course, in as-sold form, an apparatus as just described may be devoid of the battery (and the same way in some instances apply to the transformer) and apparatus of such form are to be understood as included within the scope of the invention.

Switch means will conveniently be provided in circuit with the electrode, in general between the power supply means and the transformer in the case of the preferred embodiment described above. A cut out to isolate the electrode in the event of an abnormally high current flow can be provided.

The electrode in any of the forms of the invention described above may preferably take the form of a needle-like probe or some other type of electrode disposed for direct skin contact in use of the device.

BRIEF DESCRIPTION OF THE DRAWINGS

The following is a description, by way of example only, intended to illustrate the invention, reference being made to the accompanying drawings in which:

FIG. 5 comprising views

FIG. 7 comprising views FIG. 8 comprising views

DETAILED DESCRIPTION OF THE PREFERRED EMBODIMENTS

Figure 1:
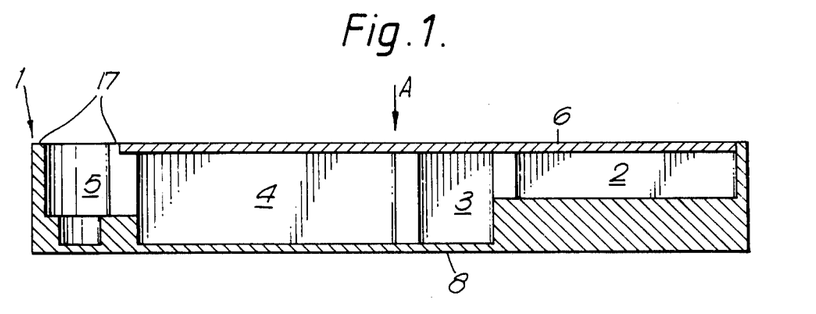
FIG. 1 is cross-sectional view of a device forming a preferred embodiment of the invention with the working parts removed for the sake of simplicity.
Figure 2:
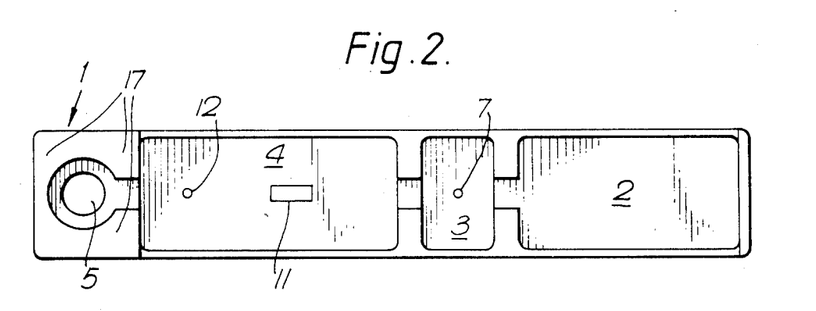
FIG. 2 is a plan view from the direction of the arrow A of FIG. 1.

The device shown in FIG. 1 comprises an elongate timber block 1 of rectangular cross-section. The block 1 has four recesses 2, 3, 4 and 5 formed in its upper surface by wood working machinery. A cover plate 6 (not shown in FIG. 2) covers recesses 2, 3 and 4.

Recess 2 is provided to receive a battery (not shown) which is a proprietary 9 v dry cell.

Recess 3 remains essentially vacant in the assembled device and is provided simply as a convenient means of connecting earth contact (not shown) exposed for skin contact through aperture 7 in the undersurface 8 of block 1 in the electrical circuit of the device.

Figure 4:
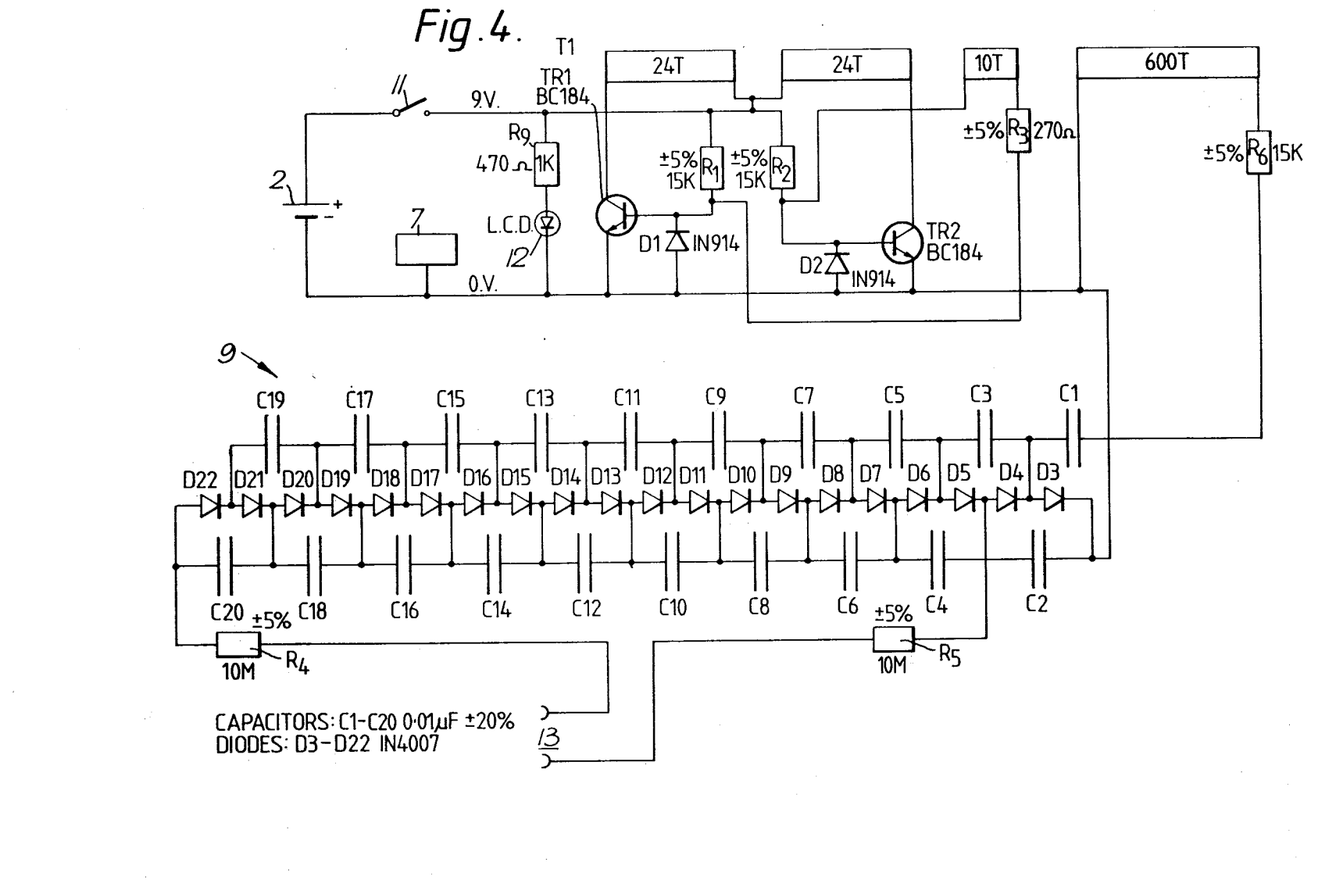
FIG. 4 is an electrical circuit diagram of the device shown in FIG. 1.

Recess 4 houses transformer not shown in FIG. 1 but indicated generally by the reference numeral 9 in FIG. 4. Two apertures 11 and 12 perforate the base of recess 4 and receive, respectively, a switch and neon indicator light (both not shown).

A corona discharge probe 13 is received in recess 5 and is connected electrically in circuit with the transformer.

Figure 3:
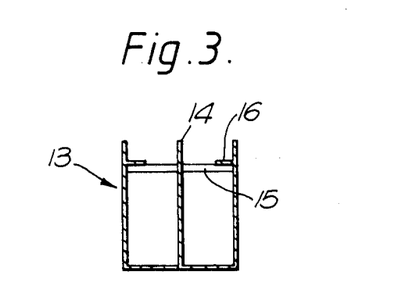
FIG. 3 is a cross-sectional view of a discharge electrode assembly as received in a fully assembled device.

Probe 13 comprises a needle-like electrode 14 which penetrates a plastics disc 15 which carries a copper annulus 16 proximate its periphery. In the assembled device, probe 13 is received in recess 5 so that the outward tip of electrode 14 lies in or just behind the plane of skin contact surface 17 of the upper surface of block 1. In this way, the electrode 14 can be brought into electrical contact with the skin of a patient by placing the skin contact surface 17 upon the skin of the patient.

In use with the device switched on at the switch and the earth contact connected to earth as through the patient's body the electrode 14 will assume a negative electric charge. An electrical arc (of voltage for example, between 1000 and 5000 volts, say 2000 volts, and current of, for example 1 μA) discharges to the patient's skin. This discharge has been found through experiment to be most beneficial. Many so called incurable physical ailments are caused by an electrical imbalance produced by a increase in acidity, resulting in an abnormal increase of positive ions, which cause pain, inflamation and muscular disability. This electrical balance cannot be restored by chemical means or by drugs. It can only be restored by introducing electrons. The body's supply of electrons is obtained from the breakdown of the atmospheric gases oxygen, nitrogen and hydrogen. Oxygen may or may not be available in the diseased tissue and even if it is available this in itself is no guarantee of activation. The foregoing provides a miniature instrument capable of safely supplying electrons to the body by directly introducing them into the skin. One application of the invention is the relief of the symptoms of arthritis and other inflammatory ailments and the assignment in their cure. Considerable effectiveness has been achieved in the relief of neuralgic pain and in the promotion of peripheral tissue renewal after burning and scalding. Therapy practiced by use of the device also finds use in connection with botanicallly and insect inflicted stings in particular bee and wasp stings and in muscular restoration.

A parts list for the circuit of FIG. 4 is shown below:

| ITEM | SUPPLIER | QTY |
| --- | --- | --- |
| 9 v battery (rechargeable) |  | 1 |
| TRI Transistor BC182 | Camtec | 2 |
| $D_1D_2$ Diode IN4148 | Camtec | 2 |
| $D_3$-$D_{22}$ Diode IN4007 | Camtec | 10 |
| Inverter Transformer RM10 | R/S | 1 |
| Enamelled Copper Wire | R/S | A/R |
| $R_1,R_2,R_6$ Resistor 15K$\Omega\frac{1}{4}$w | R/S | 3 |
| $R_3$ Resistor 270$\Omega\frac{1}{4}$w | R/S | 1 |
| $R_4,R_5$ Resistor 10 M$\Omega$ | R/S | 2 |
| $R_9$ Resistor 470$\Omega$ | R/S | 1 |
| Capacitors Ceramic $C_1$-$C_{20}$ .01 $\mu$F/1000 v | R/S | 20 |
| Test Probe | R/S | 1 |
| Battery Clip | R/S | 1 |
| P.C.B.'A' | Minnitron | 1 |
| P.C.B.'B' | Minnitron |  |
| Nylon Ring | Mr. Head | 1 |
| Push Button | R/S | 1 |
| LED. Red | R/S | 1 |
| Earthing Stud | Mr. Head | 1 |
| Case | Mr. Head |  |

Various modifications of the above-described device are contemplated as future developments. In particular, the main body of the device (the grippable member) is likely to be replaced by a moulded plastics body which will be formed to faciliate easier grasping by the hand (in particular, without the rectangular cross-section shown in FIGS. 1 and 2). The probe 13 may be a probe without corona discharge characteristics (i.e. omission of annulus 16) although the local atmospheric ionization achieved by possession of such characteristics is conductive to propagation of charge from electrode 14 into the skin.

Figure 6:
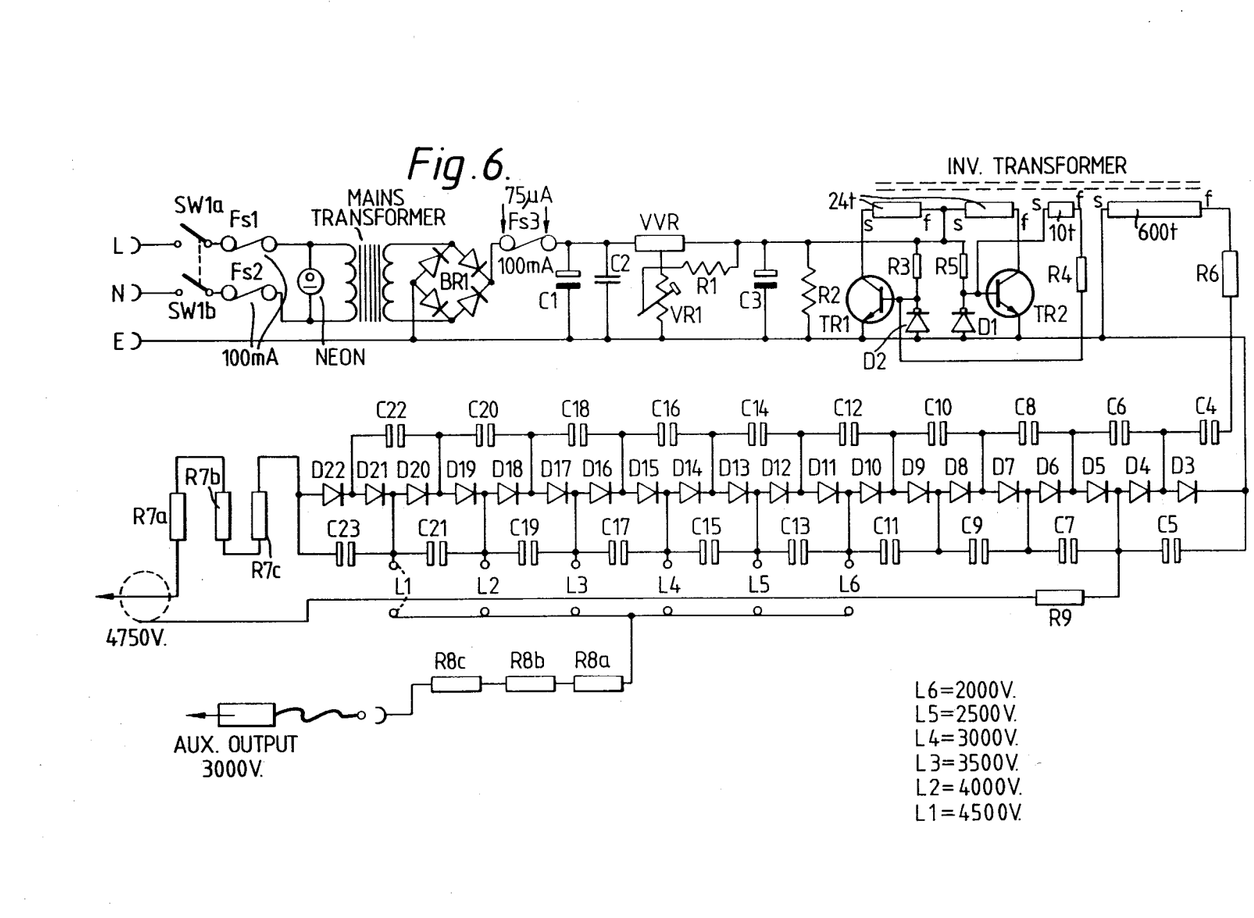
FIG. 6 is an alternative electrical circuit diagram.

A modified form of the device (shown in FIGS. 7a and 7b) just described comprises a housing having a head connected to a terminal electrode for direct skin contact in what can conventionally be termed non-invasive acupuncture, the therapy provided thereby being similar to acupuncture but involving charge propagation into the anatomy (e.g. to nerve points) without tissue perforation. An electrical circuit for this form of device is shown in FIG. 6. The parts list for the FIG. 6 circuit is set out below:

| M.K. IV | | |
| --- | --- | --- |
| ITEM | SUPPLIER | QTY |
| Aux Probe Wire | R/S (388-237) | 1 mtr |
| Mains Wire White | R/S (377-962) | 2 mtr |
| Mains transformer 9511 | Clairtronics | 1 off |
| $TR_1,TR_2$ Transistor BC 182 | Camtec | 2 off |
| $D_1D_2$ Diode IN4148 | Camtec | 2 off |
| $D_3$-$D_{22}$ Diode IN4007 | Camtec | 20 off |
| Inverter Transformer RM10 | R/S (228-258) | 1 off |
| Enamelled Copper Wire | R/S (357-918) | A/R |
| $VR_1$ 5K$\Omega$ adjustable |  |  |
| $R_3R_5$ Resistor 15K$\Omega\frac{1}{4}$w | Camtec | 2 off |
| $R_4$ Resistor 270$\Omega\frac{1}{4}$w | Camtec | 1 off |
| $R_1$ Resistor 510$\Omega\frac{1}{4}$w | Camtec | 1 off |
| $R_{7a}$-$R_{8'c}$ Resistor 100 M$\Omega\frac{1}{4}$w | Camtec | 1 off |
| $R_2$ Resistor 1K$\Omega\frac{1}{4}$w | Camtec | 1 off |
| $R_6$ Resistor 100 M$\Omega\frac{1}{4}$w | R/S (158-222) | 1 off |
| C1 Electrolytic 470 $\mu$F 16 v | Camtec (103-351) | 1 off |
| C3 Electrolytic 1 $\mu$F | Camtec (104-051) | 1 off |
| C2 Ceramic .1 $\mu$F 35 v | Camtec | 1 off |
| C4-C22 Ceramic .01 $\mu$F 1000 v | R/S (125-941) | 20 off |
| BRI 1A 800 v Bridge W10 | Camtec | 1 off |
| VVR Voltage Reg. 317 m | R/S (303-184) | 1 off |
| SW1 Mains Switch | R/S (316-888) | 1 off |
| F33 P.C.B. Fuse Holder | R/S (412-784) | 6 off |
| Fuse 100 mA | R/S (412-100) | 2 off |
| Fuse 160 mA | R/S (413-052) | 1 off |
| 4 mm Socket Red | R/S (444-646) | 1 off |
| 4 mm Socket Black | R/S (444-618) | 1 off |
| 4 mm Socket Green | R/S (444-630) | 1 off |
| Neon Indicator | R/S (577-608) | 1 off |
| Test Probe Sprung | R/S (434-324) | 2 off |
| Terminal Block | R/S (423-762) | 1 off |
| 4 mm Plug Black | R/S (444-179) | 1 off |
| 4 mm Plug Red | R/S (444-208) | 1 off |
| Front Panel | T.E.C.A | 1 off |
| P.B.C. Main | Minnitronics | 1 off |
| P.B.C. Ring | Minnitronics | 2 off |
| Perspex Assemblies | T.E.C.A. | 1 off |
| Nylon Rings |  | 2 off |
| 13 amp Plug |  | 1 off |
| Spade Terminals | R/S (533-005) | 4 off |
| Nuts and Bolts | R/S (524-039) | A/R |
| Sleeving H/S & Rubber | R/S | A/R |
| Rubber Feet | R/S (543-254) | 4 off |
| Internal Wire | R/S | A/R |
| Harwin Pins | R/S (433-854) | A/R |
| Varnish | R/S (555-550) | A/R |
| Case | Mr. Head |  |
| Mains Grommet | R/S (543-872) | 1 off |
| 5k Preset | R/S (186-738) | 1 off |

The electrical circuitry is encapsulated in resin for insulation purposes. The negative electrode of the "bioelectron" is at 3 kV d.c. and so the d.c. resistivity and electrical-stress capability of the resin should be compatible with this. The transformer gives an output of 400 volts peak-to-peak at a frequency of around 50 kHz. As the voltage multiplier takes the form of a series of half-wave rectifiers then the 3 kV d.c. output will contain a 50 kHz ripple of up to 400 Volts amplitude.

The following specifications apply to the resin materials Crystic 17449 and 199:

| Crystic 17449 | Crystic 199 |
| --- | --- |
| Tan $\delta$ = 0.018 (at $10^6$ Hz) | Tan $\delta$ = 0.005 (at $10^3$ Hz) |
| Dielectric constant K = 3.12 | Dielectric constant K = 3.1 |

At any frequency f Hz the resistivity of a material is given by $$=(2f\epsilon_o K \text{ Tan})^{-1}=1.8\times10^{12}(f K \text{ Tan})^{-1} \text{ ohm.cm}$$

For materials such as these which exhibit a weak and broad electrical loss peak, then for the frequency range 1 Hz to $10^6$ Hz the resistivity will vary with frequency according to the relationship $$=\epsilon_o f^{-1.0}$$

Using the data given above and these two equations, then the following resistivity values can be derived for the two resin types:

| Crystic 17449 | Crystic 199 |
| --- | --- |
| Tan δ = 0.018 (at $10^6$ Hz) | Tan δ = 0.005 (at $10^3$ Hz) |
| Dielectric | Dielectric |
| constant K = 3.12 | constant K = 3.1 |

At any frequency f Hz the resistivity $\rho$ of a material is given by $$\rho=(2\pi f\epsilon_o K \text{ Tan } \zeta)^{-1}=1.8\times10^{12}(f K \text{ Tan } \zeta)^{-1} \text{ ohm.cm}$$

For materials such as these which exhibit a weak and broad dielectric loss peak, then for the frequency range 1 Hz to $10^6$ Hz the resistivity will vary with frequency according to the relationship $$\rho=\rho_o f^{-1.0}$$

Using the data given above and these two equations, then the following resistivity values can be derived for the two resin types:

| Crystic 17449 | Crystic 199 |
| --- | --- |
| Resistivity at 1 Hz = 3.2 × $10^{13}$ ohm · cm | 1.2 × $10^{14}$ ohm · cm |
| Resistivity at 50 kHz = 6.4 × $10^8$ ohm · cm | 2.4 × $10^9$ ohm · cm |

The resistivity at 1 Hz can be taken to approximate (on the safe side) the d.c. resistivity, and these values will be maintained for electric field stresses up to at least $5\times10^3$ volts/cm. At such a stress the current density ($1.6\times10^{-10}$ amp/cm$^2$ and $4.2\times10^{-11}$ amp/cm$^2$ for Crystic 17449 and 199 respectively) will be negligible with respect to the 3 kV potential. At the same electrical stress than 50 kHz rms currents will be $5.5\times10^{-6}$ amp/cm$^2$ and $1.5\times10^{-6}$ amp/cm$^2$ for Crystic 17449 and 199, respectively.

Crystic 199 has the slightly better electrical insulating properties, although either resin will be completely adequate for the purpose of providing electrical insulation for the circuitry. If Crystic 199 is used with a resin insulation thickness of not less than around 2.5 mm, then the d.c. leakage current will be less than $10^{-9}$ amp/cm$^2$ and the 50 kHz leakage current will be less than $10^{-6}$ amp/cm$^2$.

The circuitry provides a series resistance of $3\times10^7$ ohm at the 3 kV electrode, which limits the short-circuit current flow to 100 microamperes at d.c. and to about 10 microamperes for the 50 kHz ripple. Such currents are physiologically safe (the threshold of sensation is about 2000 microamperes d.c.).

Figure 7A:
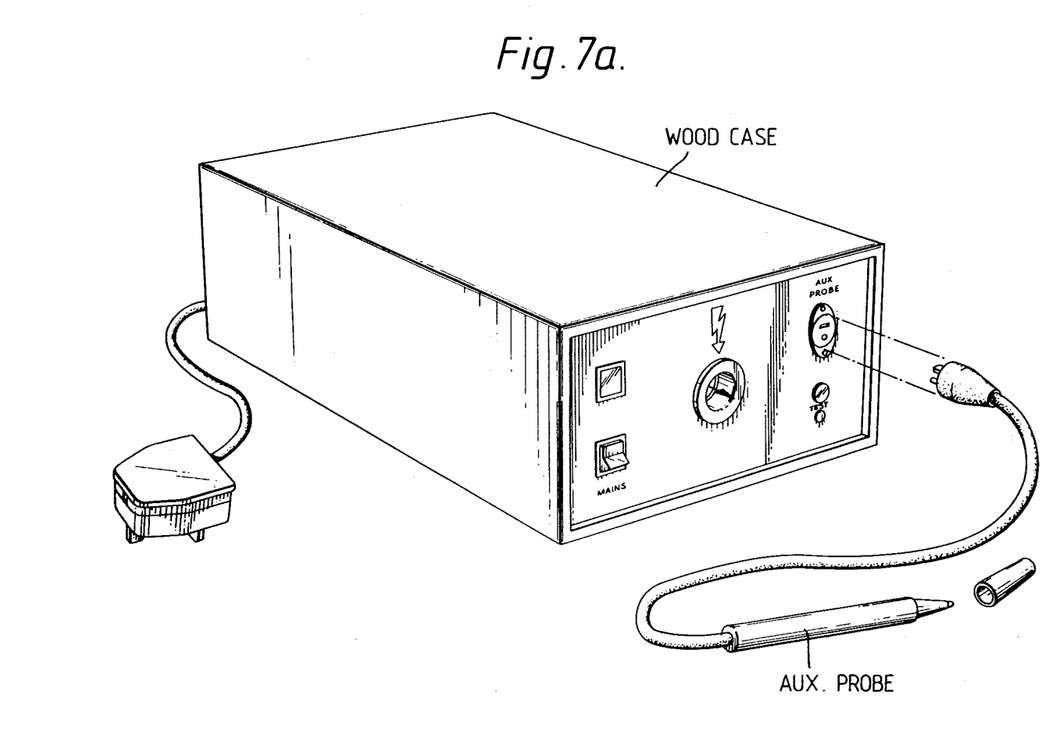
FIGS. 7a and 7b represent another device constructed in accordance with the invention.
Figure 7B:
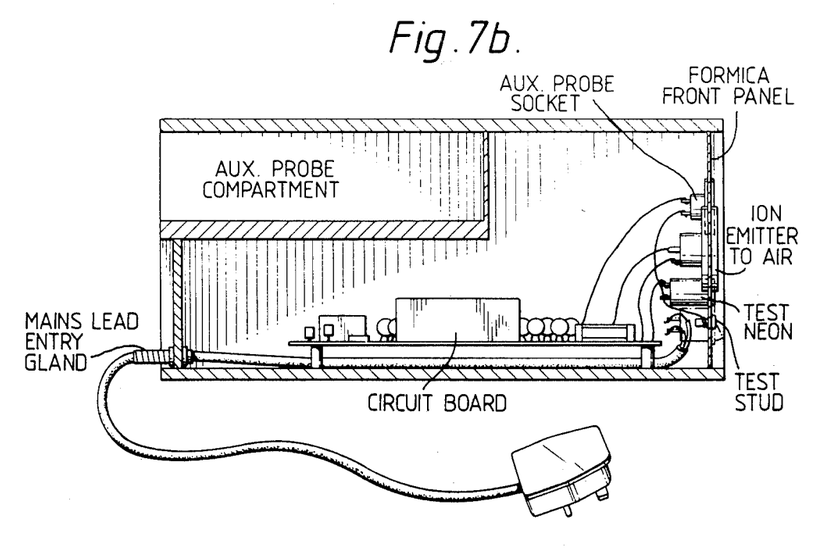
Figure 8A:
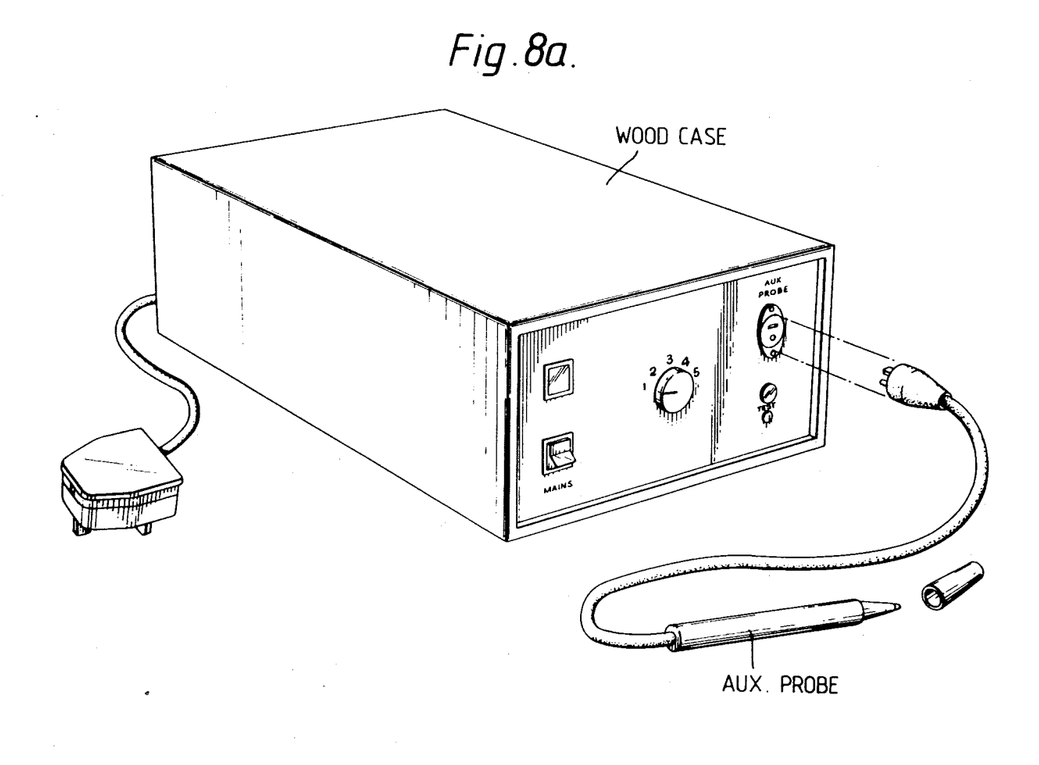
FIGS. 8a and 8b represent a further device constructed in accordance with the invention.
Figure 8B:
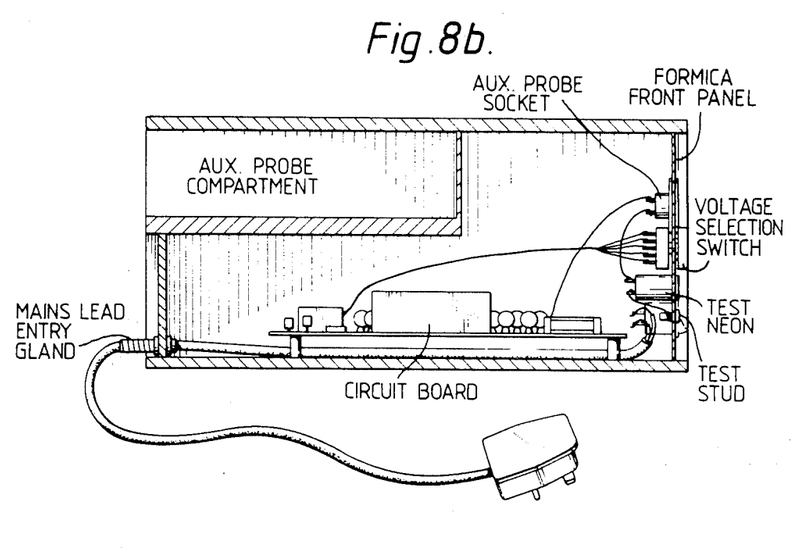

A variation of the device shown in FIGS. 7a and 7b is shown in FIGS. 8a and 8b (the circuitry being as shown in FIG. 6).

Figure 5A:
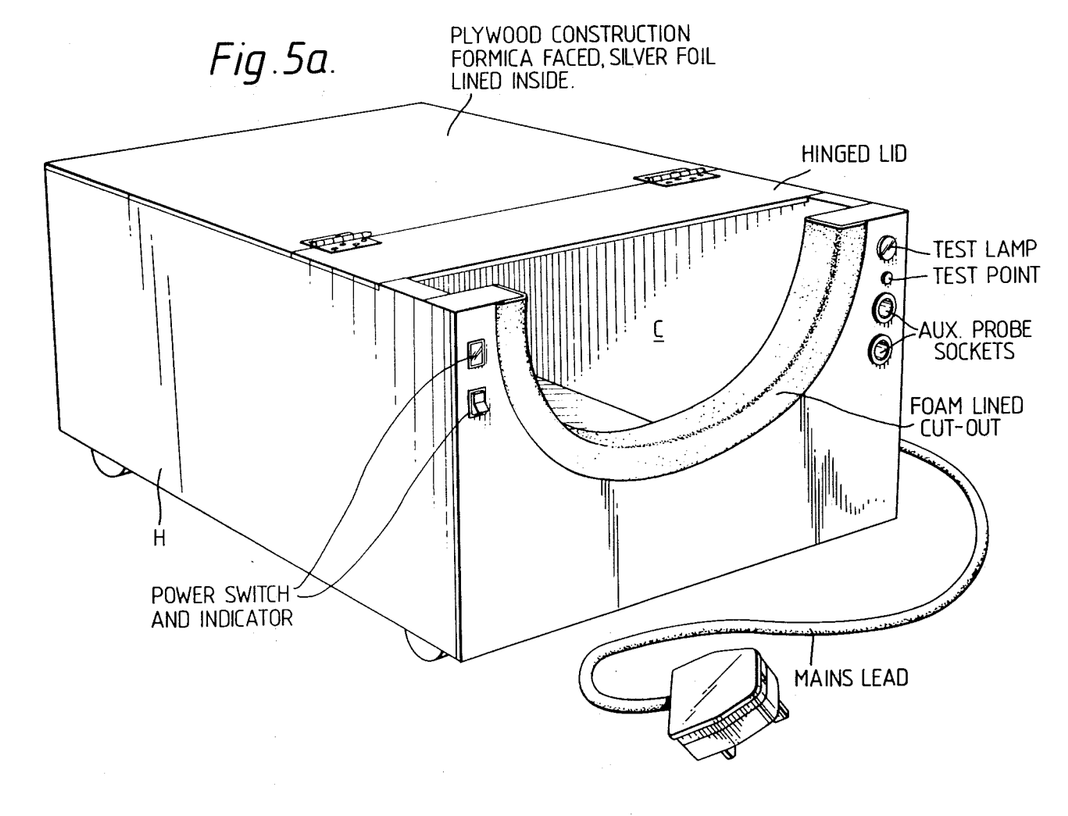
FIGS. 5a and 5b represent a modified device constructed in accordance with the invention.
Figure 5B:
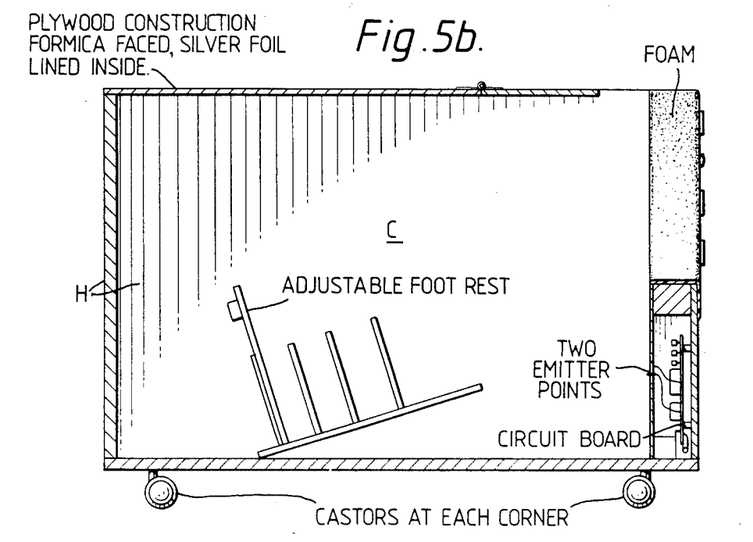

A further modification is shown in FIG. 5 the device shown using the FIG. 6 circuit without microencapsulation. In use, an anatomical part (e.g. one or more limbs—e.g. a leg) is placed in the cavity C of the housing H. Electrical charge from the emitter parts of the circuit produces atmospheric ionization which is concentrated in the region of the anatomy by the enclosing walls of the housing.

I claim:

1. An electrical therapy apparatus for anatomical applications, comprising; means for producing at an output thereof a high negative voltage between −1000 and −5000 volts, and a direct current of less than 1 mA; and a probe connected to said high negative voltage output, said probe being formed so as to pass electrons from said probe into a contacting or closely juxtaposed part of the anatomy adjacent said probe, wherein said probe comprises an electrode extending from a corona discharge ring.

2. Apparatus as claimed in claim 1, wherein, in use, the electrode is in skin contact or in close juxtaposition to the skin so as to introduce the electrons substantially completely into the anatomy.

3. Apparatus as claimed in claim 2, wherein said voltage is at least −2000 volt.

4. Apparatus as claimed in claim 1, wherein said current is less than 0.5 mA.

5. Apparatus as claimed in claim 4, wherein said current is less than 0.1 mA.

6. Apparatus as claimed in claim 4, wherein said current is between 0.005 and 0.05 mA.

7. Apparatus as claimed in claim 1, in which the high voltage producing means includes a transformer and an oscillator.

8. Apparatus as claimed in claim 7, in which the output of the transformer/oscillator is connected to voltage multiplier means.

9. Apparatus as claimed in claim 1, in which the outside of the apparatus incorporates an earth contact which may be contacted by a finger in operating the apparatus.

10. Apparatus as claimed in claim 1, including a power supply comprising a battery.

* * * * *